US 9,499,927 B2

(12) United States Patent
Simons et al.

(10) Patent No.: US 9,499,927 B2
(45) Date of Patent: Nov. 22, 2016

(54) METHOD FOR PRODUCING A PROSTHESIS FOR REINFORCING THE ABDOMINAL WALL

(71) Applicant: Sofradim Production, Trévoux (FR)

(72) Inventors: Damien Simons, Lyons (FR); Alfredo Meneghin, Laval (FR)

(73) Assignee: Sofradim Production, Trevoux (FR)

( * ) Notice: Subject to any disclaimer, the term of this patent is extended or adjusted under 35 U.S.C. 154(b) by 99 days.

(21) Appl. No.: 14/421,222

(22) PCT Filed: Sep. 25, 2013

(86) PCT No.: PCT/EP2013/069953
§ 371 (c)(1),
(2) Date: Feb. 12, 2015

(87) PCT Pub. No.: WO2014/048981
PCT Pub. Date: Apr. 3, 2014

(65) Prior Publication Data
US 2015/0218738 A1    Aug. 6, 2015

(30) Foreign Application Priority Data

Sep. 25, 2012   (FR) .................................. 12 58973

(51) Int. Cl.
*D04B 21/12*    (2006.01)
*D06B 1/00*     (2006.01)
*D06C 7/00*     (2006.01)

(52) U.S. Cl.
CPC ............. *D04B 21/12* (2013.01); *D06B 1/00* (2013.01); *D06C 7/00* (2013.01); *D10B 2403/0113* (2013.01); *D10B 2509/08* (2013.01)

(58) Field of Classification Search
CPC .................. D04B 21/02; D04B 21/04; D04B 21/06; D04B 21/08; D04B 21/10;
(Continued)

(56) References Cited

U.S. PATENT DOCUMENTS 1,187,158 A    6/1916   Mcginley
3,118,294 A    1/1964   Van Laethem
(Continued)

FOREIGN PATENT DOCUMENTS

CA    1317836 C      5/1993
DE    19544162 C1    4/1997
(Continued)

OTHER PUBLICATIONS

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).
(Continued)

*Primary Examiner* — Danny Worrell

(57) ABSTRACT

The invention relates to a method for producing a prosthesis comprising a knitted structure made in one piece, in which method a knit (1) comprising a base sheet (2) and a succession of perpendicular folds (3) is produced in a single knitting step, and said knit (1) is then cut on each side of said folds (3) in order to obtain said knitted structure.

21 Claims, 2 Drawing Sheets

Figure 1A:
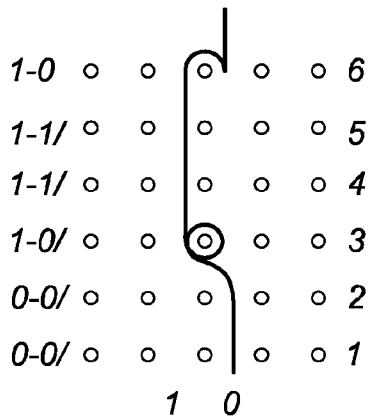

(58) Field of Classification Search
CPC ............... D04B 21/12; D04B 21/20; D04B 21/202
See application file for complete search history.

(56) References Cited

U.S. PATENT DOCUMENTS

| | | | |
|---|---|---|---|
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,888,964 A | 12/1989 | Klinge |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |

(56) References Cited

U.S. PATENT DOCUMENTS

| | | | |
|---|---|---|---|
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,113,623 A * | 9/2000 | Sgro ................. A61B 17/0057 606/151 |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Muller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,743,435 B2 | 6/2004 | DeVore et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 * | 12/2005 | Therin .................. A61F 2/0045 66/170 |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,021,086 B2 * | 4/2006 | Ory .......................... D04B 1/12 66/195 |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 8,142,515 B2 | 3/2012 | Therin et al. |
| 8,181,491 B2 * | 5/2012 | Meneghin ............. A61F 2/0045 66/195 |
| 8,197,837 B2 | 6/2012 | Jamiolkowski et al. |
| 8,323,675 B2 | 12/2012 | Greenawalt |
| 8,366,787 B2 | 2/2013 | Brown et al. |
| 8,709,094 B2 | 4/2014 | Stad et al. |
| 8,746,014 B2 * | 6/2014 | Mortarino ............. A61F 2/0063 66/170 |

(56) References Cited

U.S. PATENT DOCUMENTS

| | | |
|---|---|---|
| 8,834,864 B2 | 9/2014 | Odar et al. |
| 8,846,060 B2 | 9/2014 | Archibald et al. |
| 8,877,233 B2 | 11/2014 | Obermiller et al. |
| 8,956,373 B2 | 2/2015 | Ford et al. |
| 9,034,357 B2 | 5/2015 | Stopek |
| 2002/0095218 A1 | 7/2002 | Carr et al. |
| 2003/0086975 A1 | 5/2003 | Ringeisen |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2007/0299538 A1 | 12/2007 | Roeber |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2715405 A1 | 7/1995 |
| FR | 2 724 563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 1 454 257 A | 11/1976 |
| GB | 2 051 153 A | 1/1981 |
| JP | H0332677 A | 2/1991 |
| JP | H05237128 A | 9/1993 |
| JP | H09137380 A | 5/1997 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 02/007648 A1 | 1/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | WO 2006/092159 A1 | 9/2006 |
| WO | 2007048099 A2 | 4/2007 |
| WO | 2009031035 A2 | 3/2009 |
| WO | 2009071998 A2 | 6/2009 |

OTHER PUBLICATIONS

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

(56) References Cited

OTHER PUBLICATIONS

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyaginsteva, T. et al., "Inhibition of complement activation by water-soluble polysaccharides of some far-eastern grown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 113-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Preliminary Search Report from French Patent Office dated Dec. 20, 2006, 3 pages.
International Search Report for PCT/EP13/069953 date of completion is Dec. 19, 2013 (2 pages).

\* cited by examiner

METHOD FOR PRODUCING A PROSTHESIS FOR REINFORCING THE ABDOMINAL WALL

CROSS-REFERENCE TO RELATED APPLICATIONS

This application is a National Stage Application of PCT/EP13/069953 under 35USC §371 (a), which claims priority of French Patent Application Serial No. 12/58973 filed Sep. 25, 2012, the disclosures of each of the above-identified applications are hereby incorporated by reference in their entirety.

The present invention relates to a method for producing a prosthesis for reinforcing an abdominal wall in which an incision has been made, said prosthesis being formed from a T-shaped knitted structure made in one piece.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. A hernia of this kind can occur on a parietal scar following surgery and is then called an incisional hernia. An incisional hernia shows itself in the form of a bulge at the surface of the skin, and its reduction necessitates a further surgical intervention.

Following a surgical intervention that required an incision of the abdominal wall, for example in vascular or gynaecological surgery, it is therefore important that the closure of the incision made in the abdominal wall is optimal, so as to reduce the risks of future occurrence of an incisional hernia. With this in mind, it is desirable to be able to reinforce the abdominal wall, and in particular the muscles thereof, at the site where the suture has been made to close the incision.

In the field of prevention or repair of hernias in general, prostheses exist which comprise, for example, a first sheet of material intended to plug the hernial defect, and a second sheet of material intended to be placed in contact with the viscera, the first and second sheets being substantially perpendicular to each other, such that a transverse cross section of the prosthesis generally forms a T shape, one sheet forming the vertical bar of the T, the other sheet forming the horizontal bar of the T.

These sheets of material can be openworked. In the present application, "openworked material" is understood as meaning that the material has openings or pores at its surface and within its body. An openworked material promotes cell recolonization once the prosthesis has been implanted.

The existing T-shaped prostheses are generally produced from two separate sheets, which are subsequently joined to each other to obtain said T shape. Thus, the method of producing these existing prostheses is long-winded and complicated. The two sheets of material can be joined, for example, by sewing or else by a thermal welding means. However, particularly when these sheets are made of openworked material, such joining means may create a weakness of the prosthesis, for example a point of weakness at the join between the two sheets of material. Once implanted, the prosthesis is subjected to various pressures and/or tensions, for example by the abdominal cavity or by the muscles of the abdominal wall, which pressures and/or tensions are generated by the movements and/or efforts made by the patient in his or her daily routine. This point of weakness could therefore prove dangerous for the patient in the event of tearing.

Moreover, every solution for joining the first sheet of material to the second sheet of material in the existing prostheses, by adding a foreign material to the prosthesis or by modifying the chemical structure of the prosthesis by a thermal or mechanical process, is susceptible of creating a discontinuity in the performance of the prosthesis as a whole, and such discontinuity is undesirable.

There is still therefore a need for a reinforcement prosthesis that would comprise a skeleton of which the transverse cross section would generally form a T, hereinafter referred to for simplicity as a "T-shaped" skeleton, structure or prosthesis, having no area of weakness at the join between the vertical bar and the horizontal bar of the T.

There is also still a need for a method allowing simple and rapid production of such a T-shaped skeleton made of openworked material from which it would be possible to produce such a reinforcement prosthesis, having a continuous strength throughout the prosthesis, without any area of weakness at the join between the vertical bar and the horizontal bar of the T.

The present invention aims to meet this need by making available a prosthesis for reinforcing an abdominal wall in which an incision has been made, said prosthesis comprising a knitted structure made in one piece, said knitted structure comprising a first portion, which is substantially plane and flexible and is intended to be placed between the abdominal wall and the abdominal cavity, and a second portion, which is substantially plane and flexible and is intended to be placed between the two margins of the incision, said second portion extending substantially perpendicularly from one face of said first portion.

The present invention also relates to a method for producing such a prosthesis, said method comprising the following steps:

a) producing a knit comprising a base sheet which is substantially plane and elongate and which is equipped in its longitudinal direction with a succession of folds substantially perpendicular to said sheet, by knitting biocompatible yarns on a warp knitting machine, said yarns being distributed on at least three guide bars B1, B2 and B3, said three bars operating according to a defined weave repeat recurring as desired along the production length of the knit, each bar being supplied with a yarn coming from a corresponding warp beam rod at a dedicated run-in appropriate to the movement of said bar in accordance with said weave repeat, at least bar B1 having a variable dedicated run-in D1, the value of said variable dedicated run-in D1 decreasing and tending towards 0 on a part of said weave repeat, the decrease in the value of said run-in D1 on said part of said weave repeat generating a said perpendicular fold, b) cutting from the knit obtained in step a) a knitted structure comprising a part of said base sheet equipped with a perpendicular fold, said part of the base sheet forming said first portion of the prosthesis, and said perpendicular fold forming said second portion of the prosthesis.

The knitted structure forming the T-shaped skeleton of the prosthesis according to the invention is made in one piece, in particular in one knit, obtained in a single knitting step. In the present application, a knitted structure made in one piece is understood as meaning that said structure is produced in a single knitting step and is not formed from two or more separate pieces that are connected by a joining means, for example sewing, ultrasonic welding, etc. Thus, in the knitted structure of the prosthesis according to the invention, the yarns from which it is made present a continuity across the entire surface of the structure.

In particular, the T-shaped skeleton of the prosthesis according to the invention is not obtained by joining two sheets of material. In the prosthesis according to the invention, the first portion, which is intended to be placed between the abdominal wall and the abdominal cavity, and the second portion, which is intended to be placed between the two margins of the incision, are one and the same knit. As a result, the join between the two portions does not require any connecting means, for example sewing, thermal welding, etc. Indeed, as will become clear from the description below, it is the same yarns that form both the base sheet of the knit, in other words the first portion of the prosthesis, and also the perpendicular folds of the knit, in other words the second portion of the prosthesis.

In the present application, "plane and flexible portion" is understood as meaning that said portion has the general form of a plane textile and that it can be manipulated and deformed easily, for example in order to fold it back on itself at the time of introduction of the prosthesis into the body of a patient. Moreover, the knitted structure is formed from biocompatible yarns that have a rigidity necessary for maintaining the T shape of said knitted structure, that is to say for maintaining the perpendicular position of the second portion with respect to the first portion, in the absence of any stress exerted on a portion of said structure.

The production method according to the invention makes it possible to produce a knitted structure of which the transverse cross section has the overall shape of a T, without creating discontinuity between the first portion (horizontal bar of the T) and the second portion (vertical bar of the T) of said knitted structure.

Indeed, according to the method of the invention, a knit is produced which comprises a substantially plane base sheet provided with a succession of folds that are substantially perpendicular to said base sheet.

A warp knitting machine can comprise one or more guide bars. Each guide bar is supplied with a particular yarn that is stored in wound-up form on what is called a warp beam rod, said yarn being unwound from the warp beam rod at the rate by which it is used up in the movements of said guide bar when the latter performs its part in producing the knit according to the defined weave. In the field of knitting, the weave defines the movements of the yarns of the guide bars for forming the desired meshes in the course of production of the knit. The expression "weave repeat" applies to the basic pattern of these movements and corresponds to a defined number of meshes, the knit being produced by means of the weave repeat recurring as desired.

Corresponding to each guide bar, there is a particular yarn and a particular warp beam rod. For each combination of "guide bar/corresponding warp beam rod", the yarn is unwound from the warp beam rod at a dedicated run-in for said guide bar. Thus, each guide bar is supplied with a particular yarn at a dedicated run-in, independently of the yarns and the run-in rates of the other guide bars. The different run-in rates can be regulated by motors which can be managed by mechanical or electronic systems.

Since the production of the knit causes yarns to be used up, the respective values of the respective dedicated run-in rates of the different guide bars cannot be values less than zero and are generally positive.

By way of example, the values of the dedicated run-in rates of the guide bars in general in a warp knitting machine are generally above 1,000 mm/rack, a rack corresponding to 480 meshes.

In the present application, a "positive" value of a dedicated run-in is understood as a value of greater than or equal to 1,000 mm/rack, a rack corresponding to 480 meshes. In the present application, a value "tending towards 0" of a dedicated run-in is understood as meaning that the value of said run-in is less than or equal to 50 mm/rack, preferably less than or equal to 25 mm/rack, a rack corresponding to 480 meshes.

According to the method of the invention, the temporary decrease (temporary since only on part of the weave repeat) in the value of the variable dedicated run-in of bar B1, in such a way as to cause this value to tend towards 0, makes it possible to slow down the production of that part of the knit generated by the movement of bar B1, and a fold, said perpendicular fold, forms. However, during the time of this slowing down, all of the yarns threaded on the three bars continue to cooperate with each other to form said weave repeat, and no discontinuity forms between the fold thus generated and the base sheet of the knit.

The regulation of the run-in D1 and the variation of its value can be generated by an electronic system controlling the guide bar B1.

Thus, the prosthesis according to the invention, comprising a T-shaped knitted structure obtained from such a knit, no longer has any discontinuity in its mechanical performance between the two portions of its knitted structure, namely between the horizontal bar and the vertical bar of the T. No point or line of weakness is created in the knitted structure of the prosthesis according to the invention.

The prosthesis according to the invention thus has good strength when it is stressed in a direction perpendicular to the joining line between the two portions of its knitted structure. In the prosthesis according to the invention, the risk of tearing at the join between the two portions of the knitted structure of the prosthesis is extremely limited.

In one embodiment of the method according to the invention, each of bars B2 and B3 has a dedicated run-in (D2, D3) that is constant over the whole of said weave repeat. As has been seen above, the values of the dedicated run-in rates D2 and D3 are positive. These values can, for example, be greater than or equal to 1,000 mm/rack. For example, these values vary from 1,000 to 2,500 mm/rack, a rack corresponding to 480 meshes. The value of D2 can be different than the value of D3. Alternatively, D2 and D3 can have the same value.

Thus, during a defined period of the weave repeat, in other words during a defined number of meshes, the three bars B1, B2 and B3 are supplied with yarns according to respective positive dedicated run-in values, all of them preferably greater than or equal to 1,000 mm/rack, for example ranging from 1,000 to 2,500 mm/rack, and they form the substantially plane base sheet of the knit. Sequentially, since recurring at each new resumption of the weave repeat, the value of the dedicated run-in of bar 1 is decreased so as to tend towards 0 over part of the weave repeat, that is to say during a defined period of time corresponding to a defined number of meshes. During this defined period of time, the values of the respective dedicated run-in rates of the two other bars B2 and B3 are not decreased and they are kept constant. Thus, bars B2 and B3 continue to produce their respective parts of the knit of the base sheet. Since the latter cannot be generated in the direction of production of the knit on account of the value of the run-in D1 of bar B1 tending towards 0, it extends perpendicularly with respect to the direction of production of the knit and forms a fold. When the dedicated run-in D1 recovers its initial positive value of greater than or equal to 1,000 mm/rack, the three bars resume their respective productions of the knit in the direction of production of the knit and they again form the substantially plane base sheet.

In one embodiment of the method of the invention:
the weave repeat for bar B1 is the following: bar B1 is threaded 1 full, 3 empty according to the following chart according to the standard ISO 11676:
B1: [(0-0/0-0/1-0/1-1/1-1/1-0)×15]-(1-0)/[(0-0)×45]/0-1/1-0//
the value of the run-in D1 tending towards 0 over the part of the weave repeat [(0-0)×45],
the weave repeat for bar B2 is the following: bar B2 is threaded 1 full, 1 empty according to the following chart according to the standard ISO 11676:
B2: [1-0/2-3/2-1/2-3/1-0/1-2//]×23,
the value of the run-in D2 having a constant value over the whole of the weave repeat,
the weave repeat for bar B3 is the following: bar B3 is threaded 1 full, 1 empty according to the following chart according to the standard ISO 11676:
B3: [3-4/2-1/2-3/2-1/3-4/3-2//]×23,
the value of the run-in D3 having a constant value over the whole of the weave repeat.

Thus, in such a case, for each bar, the weave repeat comprises 138 meshes. The value of the run-in D1 of bar B1 is forced to tend towards 0 during 45 meshes (part of the weave repeat [(0-0)×45]). The perpendicular fold of the knit therefore forms during these 45 meshes, and it is formed from the yarns of bars B2 and B3 which continue to produce their respective weave repeats, determined by their respective charts shown above, during these 45 meshes.

Since the weave repeat recurs in the direction of production of the knit as the knitting machine is fed, a knit comprising a base sheet and a succession of substantially perpendicular folds is produced. Moreover, since the same weave repeat recurs every 138 meshes along the length of production of the knit, the perpendicular folds are spaced apart from one another at regular intervals.

The values given above for the charts, threadings and weave repeats have of course been given as examples. Other charts, threadings and weave repeats can be used to produce a knit comprising a base sheet provided with a succession of substantially perpendicular folds, if the value of the dedicated run-in D1 is forced to tend towards 0 on part of the weave repeat of bar B1.

To produce the prosthesis according to the invention, it then suffices to cut the resulting knit on each side of a substantially perpendicular fold in order to obtain a knitted structure made in one piece and having a T-shaped transverse cross section free of any discontinuity or weakness at the join between the vertical and horizontal bars of the T. Indeed, as will become clear from the description below, the yarns of bar B1, which join the perpendicular fold to the base sheet, are an integral part of the knit, and they are thus likewise an integral part of the knitted structure obtained by cutting as described above, by joining the vertical bar of the T to the horizontal bar of the latter.

The knitted structure of the prosthesis according to the invention is openworked. It has openings or pores at its surface and within its body, corresponding in particular to the different meshes of said knit. Such an openworked structure promotes the penetration of cells into the knitted structure and, therefore, the cell recolonization of the prosthesis after implantation.

The knitted structure can be used as it is to form a prosthesis for reinforcing the abdominal wall, or it can form part of such a reinforcement prosthesis. In particular, the knitted structure can be subjected to one or more steps that are customary in the manufacture of a prosthesis, for example thermosetting, washing, cutting, thermoforming.

In one embodiment, the knitted structure can be partially or completely coated on some or all of its faces with a coating of biocompatible material, for example anti-adhesion material. Alternatively or in addition, the knitted structure can be combined with another textile to form a composite reinforcement prosthesis.

The knitted structure is sufficiently flexible to be folded back on itself if necessary, for example at the time when introducing it into the abdominal cavity.

The knitted structure of the prosthesis according to the invention can be bioabsorbable, permanent, or partially bioabsorbable. Thus, it can be produced by knitting biocompatible yarns, for example monofilaments and/or multifilaments, made of any bioabsorbable or non-bioabsorbable biocompatible material.

In one embodiment, the knitted structure is composed of monofilament yarns. With such an embodiment, it is possible in particular to obtain a good stability of the knitted structure, in particular a good retention of its T shape, in the absence of any external stress exerted on said structure.

The monofilament yarns can have any diameter with which it is possible to obtain a knit that is suitable for the production of a prosthesis for reinforcing the abdominal wall. For example, the mean diameter of the monofilament yarns can vary from 80 μm to 200 μm.

In one embodiment of the method of the invention using bars B1, B2 and B3 and the threadings and weave repeats described above, and with said three bars B1-B3 being threaded with monofilament yarns made of one and the same biocompatible material, the monofilament yarn threaded on bar B1 has a mean diameter greater than the respective mean diameters of the monofilament yarns threaded on bars B2 and B3. Such an embodiment permits optimal continuity of the properties of strength of the two portions of the knitted structure thus obtained in the area of the joining line of said two portions. Therefore, the risks of the prosthesis, obtained from such a knitted structure, tearing after implantation, and when subjected to the pressures and forces resulting from the everyday movement of the patient, are extremely limited.

In the present application, "bioabsorbable" is understood as the characteristic by which a material is absorbed by the biological tissues and disappears in vivo after a given period which, for example, can vary from one day to several months, depending on the chemical nature of the material.

The knitted structure of the prosthesis according to the invention can be produced from yarns that are entirely bioabsorbable, in particular if it is intended to disappear after having performed its reinforcing function while cell colonization takes place and tissue rehabilitation takes over. Thus, in one embodiment, said knitted structure is composed of bioabsorbable yarns.

In other embodiments, the knitted structure can comprise non-bioabsorbable yarns if the prosthesis is intended to act as a permanent reinforcement and to remain definitively within the body of the patient.

Thus, the bioabsorbable materials suitable for the yarns of the knitted structure of the present invention can be chosen from among polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, copolymers thereof, and mixtures thereof. The non-bioabsorbable materials suitable for the yarns of the knitted structure of the present invention can be chosen from among polyethylene terephthalate (PET), polyamides, aramids, expanded polytetrafluoroethylene, polyurethane, polyvinylidene difluoride (PVDF), polybutyl esters, PEEK (polyether ether ketone), polyolefins (such as polyethylene or polypropylene), copper alloys, silver alloys, platinum, medical grades of steel such as medical-grade stainless steel, and combinations thereof.

In one embodiment, the face of said first portion intended to be placed opposite the abdominal cavity is covered by an anti-adhesion coating.

In the present application, "anti-adhesion" is understood as referring to a biocompatible material or coating that is smooth and non-porous, provides no space for cell recolonization and prevents the surrounding organs from attaching themselves to the prosthesis.

The anti-adhesion material or coating can be chosen from bioabsorbable materials, non-bioabsorbable materials and mixtures thereof.

The non-bioabsorbable anti-adhesion material can be chosen from polytetrafluoroethylene, polysiloxanes, polyurethanes, stainless steels, derivatives of precious metals, and mixtures thereof.

Said anti-adhesion material or coating is preferably bioabsorbable: the bioabsorbable materials suitable for said anti-adhesion coating can be chosen from collagens, for example oxidized collagen, oxidized celluloses, polyacrylates, trimethylene carbonates, caprolactones, dioxanones, glycolic acid, lactic acid, glycolides, lactides, polysaccharides, for example chitosans, polyglucuronic acids, hyaluronic acids, dextrans, fucans, polyethylene glycol, glycerol and mixtures thereof.

Upon implantation of the prosthesis according to the invention, the anti-adhesion coating makes it possible, at least during the initial phase of healing, to protect the knitted structure of the prosthesis at the place where this anti-adhesion coating is present; thus, the covered face is not exposed to inflammatory cells such as granulocytes, monocytes, macrophages or even the multi-nuclear giant cells that are generally activated by the surgery. Indeed, at least during the initial phase of healing, the duration of which can vary between 5 and 10 days approximately, only the anti-adhesion coating can be accessed by the various factors such as proteins, enzymes, cytokines or cells of the inflammatory line.

In the case when the anti-adhesion coating is made of non-absorbable materials, it thus protects the knitted structure before and after implantation, throughout the period of implantation of the prosthesis.

Moreover, by virtue of the anti-adhesion coating, the surrounding fragile tissues, for example the hollow viscera, are protected, in particular from the formation of undesirable and serious post-surgical fibrous adhesions.

In the case when the anti-adhesion material comprises a bioabsorbable material, it is preferable to choose a bioabsorbable material that is absorbed only after a few days, so as to ensure that the anti-adhesion coating can perform its function of protecting the surrounding organs during the days after the operation and until the cell recolonization of the prosthesis in turn protects these organs.

In one embodiment, the anti-adhesion coating is in the form of a bioabsorbable film.

Examples of methods by which the knit is covered by an anti-adhesion coating are given in the applications WO9906079 and WO9906080.

Figure 1B:
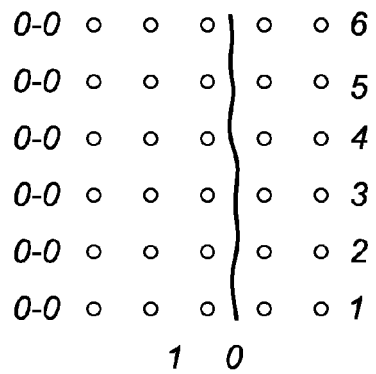
Figure 1C:
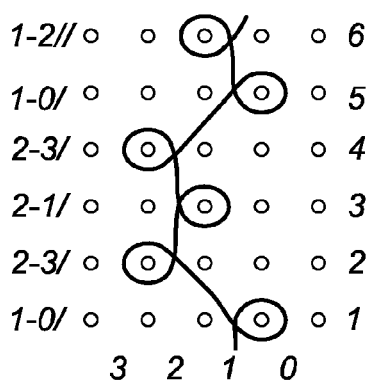
Figure 1D:
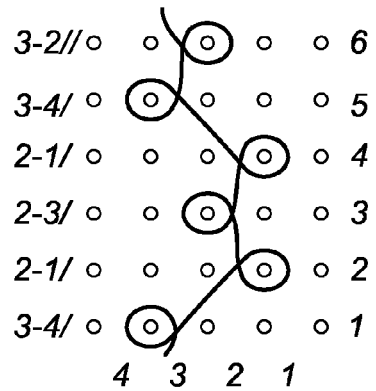
Figure 2:
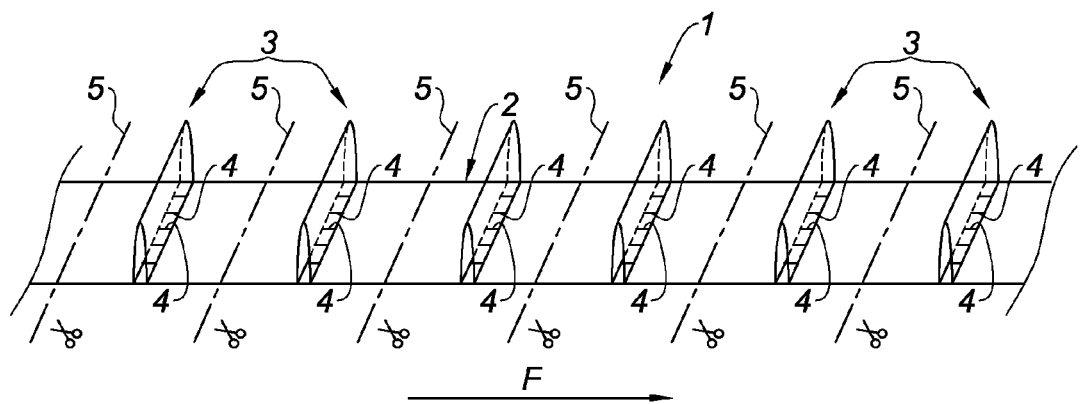
Figure 3:
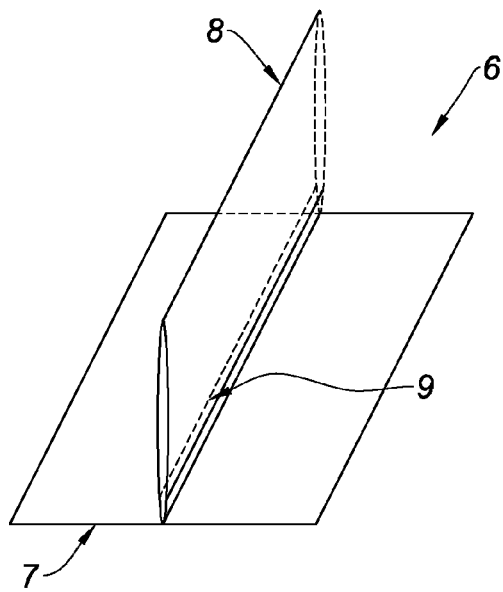
Figure 4:
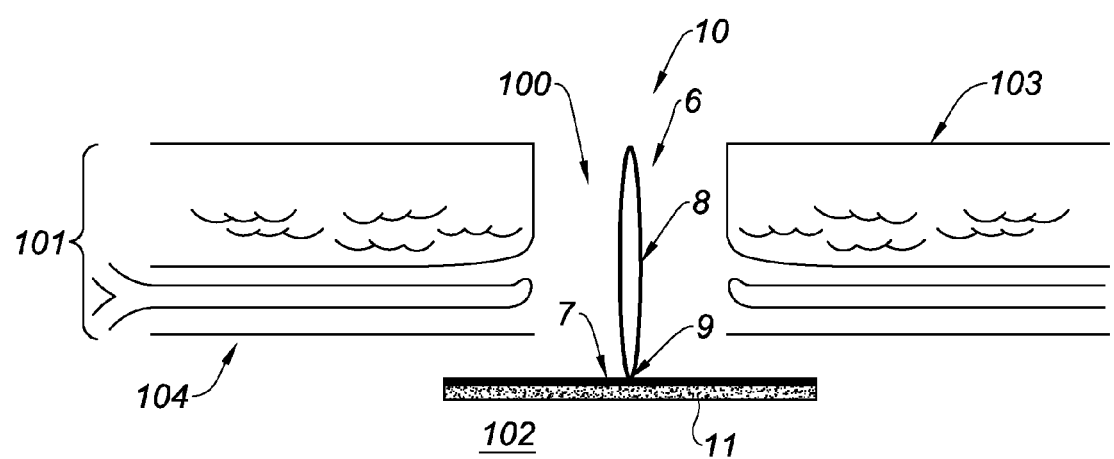

The advantages of the present invention will become clearer from the following description and example and from the attached drawings, in which:

FIGS. 1A and 1B are representations of the charts of the weave repeat of bar B1 for implementing the method according to the invention, FIG. 1C is a representation of the chart of the weave repeat for bar B2 for implementing the method according to the invention, FIG. 1D is a representation of the chart of the weave repeat of bar B3 for implementing the method according to the invention, FIG. 2 is a diagram showing a perspective view of a knit obtained by the method according to the invention, FIG. 3 is a diagram showing a perspective view of a knitted structure of a prosthesis according to the invention, FIG. 4 is a cross-sectional view of a prosthesis according to the invention in place within an incision in an abdominal wall that is to be closed.

EXAMPLE

A knit comprising a base sheet and a succession of substantially perpendicular folds is produced by the method according to the invention on a warp knitting machine with three guide bars B1, B2 and B3, such as those described above, where bar B1 is in position 1 on the knitting machine, bar B2 is in position 2, and bar B3 is in position 3. The threading, the run-in rates, the weaves and the charts are the following, in accordance with the standard ISO 11676:

B1: [(0-0/0-0/1-0/1-1/1-1/1-0)×15]-(1-0)/[(0-0)×45]/0-1/1-0//

Bar B1 is threaded 1 full, 3 empty, its dedicated run-in D1 is variable: thus, the value of D1 is positive and constant, in other words ranging from 1,000 to 2,500 mm/rack, a rack corresponding to 480 meshes, on a first part of the weave repeat, namely on the part [(0-0/0-0/1-0/1-1/1-1/1-0)×15]. Then this value decreases and tends towards zero on the part of the weave repeat [(0-0)×45].

The yarn threaded on bar B1 is, for example, a monofilament yarn of polylactic acid (PLA) having a mean diameter of 150 μm.

B2: [1-0/2-3/2-1/2-3/1-0/1-2//]×23

Bar B2 is threaded 1 full, 1 empty, its dedicated run-in D2 has a positive constant value, in other words ranging from 1,000 to 2,500 mm/rack, a rack corresponding to 480 meshes.

B3: [3-4/2-1/2-3/2-1/3-4/3-2//]×23

Bar B3 is threaded 1 full, 1 empty, its dedicated run-in D3 has a positive constant value, in other words ranging from 1,000 to 2,500 mm/rack, a rack corresponding to 480 meshes.

The yarns threaded on the bars B2 and B3 are, for example, monofilament yarns of polylactic acid (PLA) having a mean diameter of 80 μm.

Thus, the present example will result in a knit, hence a knitted structure, that is entirely bioabsorbable.

Alternatively, if the aim is to produce a permanent knit, that is to say a non-bioabsorbable knit, the yarns threaded on the three bars could be monofilaments of polyethylene terephthalate (PET).

FIG. 1A illustrates the chart, namely the movement over 6 meshes, of the yarn of bar B1 on the first part of its weave, namely on the part [(0-0/0-0/1-0/1-1/1-1/1-0)×15] on which the value of D1 is constant and positive. The movement shown in this figure for 6 meshes is repeated 15 times, over a total of 90 meshes.

FIG. 1B illustrates the movement of the yarn of bar B1 on the second part of its weave, namely on the part [(0-0)×45] on which the value of D1 tends towards 0. Indeed, on this first part of the weave, namely for 45 meshes, the yarn remains as it were in place, since it is not used up.

FIG. 1C illustrates the chart, namely the movement over 6 meshes, of the yarn of bar B2 on the whole of its weave, the value D2 being constant and positive. The movement shown in this figure for 6 meshes is repeated 23 times, on a total of 138 meshes.

FIG. 1D illustrates the chart, namely the movement over 6 meshes, of the yarn of bar B3 on the whole of its weave, the value D3 being constant and positive. The movement shown in this figure for 6 meshes is repeated 23 times, on a total of 138 meshes.

As will be clear from the above weave repeats, when the values of the three run-in rates D1, D2 and D3 are positive and constant, the chart comprises 6 meshes (numbered from 1 to 6 in FIGS. 1A, 1C and 1D). In other words, for each bar, the yarn repeats the same chart and recommences the same movement every 6 meshes.

When they are constant and positive, the values of run-in rates D1-D3 are appropriate to the respective movements of the guide bars. By way of example, these values are generally in excess of 1,000 mm/rack, a rack corresponding to 480 meshes.

Moreover, the weave repeat comprises 138 meshes. Thus, for bars B2 and B3, the same chart (6 meshes) is repeated 23 times on one weave repeat.

For bar B1, the same chart (6 meshes) is repeated 15 times, in other words on 90 meshes, with the value D1 of the dedicated speed constant and positive.

Then, after a transition mesh, the chart (0-0) is repeated 45 times, in other words on 45 meshes, with the value D1 tending towards 0. This part of the weave repeat is illustrated in FIG. 1B.

Finally, the weave repeat for bar B1 ends with two transition meshes.

Thus, during a defined period of the weave repeat, in other words during a defined number of meshes, namely on the first 90 meshes of the weave repeat in the present example, the three bars B1, B2 and B3 are supplied with yarns at dedicated run-in rates which all have constant and positive values, and which are preferably all greater than or equal to 1,000 mm/rack, and the three bars produce the substantially plane base sheet of the knit.

Then, after a transition mesh, the value of the dedicated run-in D1 of bar B1 is reduced so as to tend towards 0 across a defined number of meshes, namely 45 meshes in the present example. During these 45 meshes, the respective dedicated run-in rates of the other two bars B2 and B3 continue to produce their respective parts of the knit of the base sheet. Since the latter cannot be generated in the direction of production of the knit on account of the value of the run-in D1 of bar B1 tending towards 0, it extends perpendicularly with respect to the direction of production of the knit and forms a fold.

Once the 45 meshes have been produced, and after two transition meshes, the weave repeat is recommenced from the start. Thus, the dedicated run-in D1 resumes its initial positive value greater than or equal to 1,000 mm/rack, and the three bars resume their respective productions of the knit in the direction of production of the knit and they again form the substantially plane base sheet, until the next variation of the value of D1 and the production of the following fold.

A knit is thereby obtained which comprises a base sheet and a succession of substantially perpendicular folds. In FIG. 2, such a knit 1 is shown that has been obtained according to the method described above. The knit 1 comprises a substantially plane base sheet 2, and perpendicular folds 3 spaced apart from one another at uniform intervals corresponding to the weave repeat. This figure also shows schematically the yarns 4 of bar B1, which have not advanced in the direction of production of the knit 1, indicated by the arrow F, during the decrease in the value of D1 across the 45 meshes of the second part of the weave repeat of bar B1 as described above. As is clear from this figure, the yarns 4 form an integral part of the knit 1, and they join the base sheet 2 to the fold 3 without creating any discontinuity or area of weakness.

To produce a prosthesis according to the invention from the knit 1 obtained above, the knit 1 is then cut in the area of its base sheet 2, on each side of a perpendicular fold 3, along the cutting lines 5 indicated by dot-and-dash lines, this step being indicated schematically in FIG. 2 by the representation of a pair of scissors.

A knitted structure 6, as shown in FIG. 3, is thus obtained in one piece. This knitted structure 6 has the general shape of a T, shown upside down in this figure, and thus comprises a first portion 7, which is substantially plane and flexible and can be placed between the abdominal wall and the abdominal cavity, and a second portion 8, which is substantially plane and flexible and is intended to be placed between the two margins of a parietal incision, as will be seen in FIG. 4, said second portion 8 extending substantially perpendicularly from one face of said first portion 7.

Thus, the knitted structure 6 forming the T-shaped skeleton of the prosthesis according to the invention is made in one piece, and there is no area of weakness created at the join 9 between the first portion 7 and the second portion 8.

Moreover, the knitted structure of the present example is composed of monofilament yarns. Thus, its stability and the retention of its T shape in the absence of external stress are particularly excellent.

Moreover, the three bars B1-B3 above are all threaded with monofilament yarns of one and the same biocompatible material, namely polylactic acid (PLA), the yarns of bar B1 having a mean diameter greater than the mean diameter of the yarns of bars B2 and B3. This results in optimal continuity of the properties of strength of the two portions of the knitted structure in the area of the joining line of said two portions.

Therefore, when the knitted structure 6 is stressed mechanically in the direction of production of the knit (see FIG. 2), there is no risk of its mechanical performance dropping at the join between the first portion 7 and the second portion 8.

The knitted structure 6 can be used as it is as a prosthesis for reinforcing the abdominal wall.

The knitted structure 6 can be subjected to one or more steps that are customary in the manufacture of a prosthesis, for example thermosetting, washing, cutting, thermoforming.

In one embodiment, and with reference to FIG. 4, the prosthesis 10 according to the invention comprises a knitted structure 6 as described above which is thermoset and which is provided, on the face of the first portion 7 directed away from the second portion 8, with a layer of anti-adhesion coating 11, as shown in FIG. 4.

FIG. 4 shows an incision 100 in the abdominal wall 101, for example created for the needs of a surgical intervention. The skin 103, the abdominal wall 101 and the peritoneum 104 have been incised. Once the surgical intervention has been completed, at the time of closure of this incision 100, the surgeon introduces the prosthesis 10 into the abdominal cavity 102 and positions it so as to place the first portion 7 between the abdominal wall 101 and the abdominal cavity 102, with the anti-adhesion coating 11 opposite the abdominal cavity 102, and the second portion 8 between the two margins of the incision 100. In the prosthesis 10, the knitted structure 6 and the anti-adhesion coating 11 are sufficiently flexible to be able to be deformed when the prosthesis is introduced at the site of implantation.

The surgeon can then suture the second portion 8 of the prosthesis 10 to the muscles of the abdominal wall 101.

The prosthesis 10 thus implanted is able to reinforce the abdominal wall and reduce the risk of occurrence of a hernia after an incision has been made in the abdominal wall for the requirements of a surgical intervention. In particular, since the knitted structure 6 forming the skeleton of the prosthesis 10 is made in one piece, the prosthesis shows no discontinuity in its performance at the join between the first portion 7 and the second portion 8. Therefore, the risks of the prosthesis tearing at this join under the effect of the pressures/forces applied to the prosthesis in the direction of its width are extremely limited.

The invention claimed is:

1. A method for producing a prosthesis for reinforcing an abdominal wall in which an incision has been made, the prosthesis comprising a knitted structure made in one piece, the knitted structure comprising a first portion, which is substantially plane and flexible and is intended to be placed between the abdominal wall and the abdominal cavity, and a second portion, which is substantially plane and flexible and is intended to be placed between two margins of the incision, the second portion extending substantially perpendicularly from one face of the first portion, the method comprising the following steps:
   a) producing a knit comprising a base sheet which is substantially plane and elongate and which is equipped in a longitudinal direction with a succession of substantially perpendicular folds to the base sheet, by knitting biocompatible yarns on a warp knitting machine, the biocompatible yarns being distributed on at least three guide bars B1, B2 and B3, the three guide bars operating according to a defined weave repeat recurring as desired along a production length of the knit, each guide bar being supplied with a biocompatible yarn coming from a corresponding warp beam rod at a dedicated run-in appropriate to movement of the guide bar in accordance with the weave repeat, at least bar BI having a variable dedicated run-in value DI, wherein the variable dedicated run-in value DI decreases and tends towards 0 on a part of the weave repeat, the decrease in the variable dedicated run-in value DI on the part of the weave repeat generates a substantially perpendicular fold to the base sheet,
   b) cutting from the knit obtained in step a) a knitted structure comprising a part of the base sheet equipped with the substantially perpendicular fold, the part of the base sheet forming the first portion of the prosthesis, and the substantially perpendicular fold forming the second portion of the prosthesis.

2. The method according to claim 1, wherein each of guide bars B2 and B3 has a constant dedicated run-in value D2, D3 over a whole of the weave repeat.

3. The method according to claim 1, wherein the biocompatible yarns comprise bioabsorbable material selected from the group consisting of polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, copolymers thereof, and mixtures thereof.

4. The method according to claim 1, wherein the biocompatible yarns comprise non-bioabsorbable material selected from the group consisting of polyethylene terephthalate (PET), polyamides, aramids, expanded polytetrafluoroethylene, polyurethane, polyvinyl idene difluoride (PVDF), polybutyl esters, PEEK (polyether ether ketone), polyethylene, polypropylene, and combinations thereof.

5. The method according to claim 1, wherein guide bar B1 is threaded 1 full, 3 empty and the weave repeat of guide bar B1 is according to the following chart according to the standard ISO 11676:
   BI: [(0-0/0-0/1-0/1-1/1-1/1-0)×I5]-(1-0)/[(0-0)×45]/0-1/1-0//
   wherein the variable run-in value DI decreases and tends towards 0 over the part of the weave repeat [(0-0)×45].

6. The method according to claim 5, wherein guide bar B2 is threaded 1 full, 1 empty and the weave repeat of guide bar B2 is according to the following chart according to the standard ISO 11676:
   B2: [I-0/2-3/2-I/2-3/I-0/I-2//]×23,
   wherein a dedicated run-in value D2 of guide bar B2 is constant over a whole of the weave repeat.

7. The method according to claim 6, wherein guide bar B3 is threaded 1 full, 1 empty according to the following chart according to the standard ISO 11676:
   B3: [3-4/2-1/2-3/2-1/3-4/3-2//]×23,
   wherein a dedicated run-in value D3 of guide bar B3 is constant over the whole of the weave repeat.

8. The method according to claim 7, wherein the biocompatible yarns distributed on guide bars B1-B3 are monofilament yarns.

9. The method according to claim 8, wherein the monofilament yarn threaded on guide bar BI has a mean diameter greater than a mean diameter of each of the monofilament yarns threaded on guide bars B2 and B3.

10. The method according to claim 8, wherein the mean diameter of the monofilament yarn threaded on guide bar B1 is 150 μm and the mean diameter of each of the monofilament yarns threaded on guide bars B2 and B3 is 80 μm.

11. The method according to claim 8, wherein the monofilament yarns are made of the same biocompatible material.

12. The method according to claim 11, where the biocompatible material is polylactic acid (PLA).

13. The method according to claim 11, wherein the biocompatible material is polyethylene terephthalate (PET).

14. The method according to claim 1, wherein the substantially perpendicular folds are spaced apart at uniform intervals.

15. The method according to claim 1, wherein the biocompatible yarn of guide bar B1 joins the base sheet to the substantially perpendicular fold without creating any discontinuity or area of weakness.

16. The method according to claim 1, wherein the prosthesis comprises a one-piece, generally T-shaped knitted structure.

17. The method according to claim 1, wherein step b) comprises cutting the knit along the base sheet on each side of the perpendicular fold.

18. The method according to claim 1, further comprising subjecting the knitted structure to one or more additional steps selected from the group consisting of thermosetting, washing, cutting and thermoforming.

19. The method according to claim 1, further comprising step c) which comprises covering a face of the first portion opposite the second portion with an anti-adhesion coating.

20. The method according to claim 19, wherein the anti-adhesion coating is a bioabsorbable film.

21. The method according to claim 20, wherein the bioabsorbable film comprises collagen.

* * * * *